United States Patent

Evers et al.

[11] Patent Number: 5,126,357
[45] Date of Patent: Jun. 30, 1992

[54] ANTI-INFLAMMATORY PICOLYSELENOBENZAMIDES AND SALTS THEREOF

[75] Inventors: Michel Evers, Liege, Belgium; Michael Parnham, Pulheim, Fed. Rep. of Germany; Axel Römer, Hürth-Gleuel, Fed. Rep. of Germany; Hartmut Fischer, Cologne, Fed. Rep. of Germany; Norbert Dereu, Hürth, Fed. Rep. of Germany

[73] Assignee: A. Nattermann & Cie. GmbH, Cologne, Fed. Rep. of Germany

[21] Appl. No.: 611,274

[22] Filed: Nov. 8, 1990

[30] Foreign Application Priority Data

Nov. 8, 1989 [DE] Fed. Rep. of Germany ....... 3937171

[51] Int. Cl.$^5$ ............... A61K 31/44; C07D 213/40; C07D 213/75
[52] U.S. Cl. ............... 514/332; 514/333; 514/338; 514/357; 546/256; 546/265; 546/270; 546/330; 546/337; 546/342
[58] Field of Search ............... 546/256, 265, 270, 330, 546/337, 342; 514/332, 333, 338, 357

[56] References Cited

U.S. PATENT DOCUMENTS 4,730,053  3/1988  Dereu et al. ............... 546/335

FOREIGN PATENT DOCUMENTS 3443467  5/1986  Fed. Rep. of Germany .
3626554  2/1988  Fed. Rep. of Germany .

OTHER PUBLICATIONS

Chem. Res. Toxicol. 1990, vol. 3, pp. 199–203.

*Primary Examiner*—Bernard Dentz

[57] ABSTRACT

A compound or a pharmaceutically acceptable salt thereof, having anti-inflammatory activity, is disclosed according to the Formula (I)

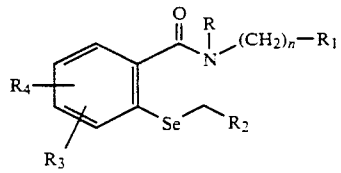

wherein
R is hydrogen, methyl or ethyl,
$R_1$ is a 2-pyridyl, 3-pyridyl or 4-pyridyl group or is phenyl, chlorophenyl or fluorophenyl,
$R_2$ is a 2-pyridyl, 3-pyridyl or 4-pyridyl group,
$R_3$ and $R_4$ are identical or different and, taken separately, are hydrogen, fluorine, chlorine, bromine, $C_1$ to $C_4$ alkyl, $C_1$ to $C_4$ alkoxy, hydroxy, cyano or nitro or, taken together, are methylenedioxy, and n is 0 or 1.

7 Claims, No Drawings

ANTI-INFLAMMATORY PICOLYSELENOBENZAMIDES AND SALTS THEREOF

FIELD OF THE INVENTION

The invention relates to novel picolylselenobenzamides and their salts, method and intermediates for their preparation and pharmaceutical products containing these compounds.

DESCRIPTION OF THE INVENTION

The compounds to which this invention relates correspond to the Formula I

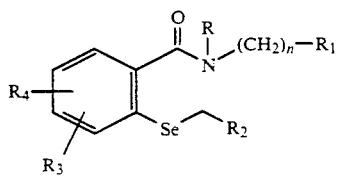

where

R is hydrogen, ethyl or methyl $R_1$ represents the pyridyl group, phenyl or substituted phenyl group, $R^2$ is the pyridyl group and $R^3$, $R^4$ are identical or different and, taken separately, represent hydrogen, fluorine, chlorine, bromine, $C_{1-4}$-alkyl, $C_{1-4}$-alkoxy, hydroxy, cyano or nitro or, taken together, methylenedioxy and n is zero or one.

Especially preferred are compounds in which n equals zero

R is hydrogen and $R_1$ represents the pyridyl group, phenyl, or substituted phenyl group, $R^2$ is the pyridyl group and $R^3$, $R^4$ are identical or different and, taken separately, represent hydrogen, fluorine, chlorine, bromine, $C_{1-4}$-alkyl, $C_{1-4}$-alkoxy, hydroxy, cyano or nitro or, taken together, methylenedioxy.

The compounds can also be in the form of their salts, preferably their pharmaceutically acceptable salts. Also especially preferred are compounds of Formula I in which N equals 1 and R is hydrogen while $R_1$ represents the pyridyl group, phenyl or substituted phenyl group, $R^2$ is the pyridyl group and $R^3$, $R^4$ are identical or different and, taken separately, represent hydrogen, fluorine, chlorine, bromine, $C_{1-4}$-alkyl, $C_{1-4}$-alkoxy, hydroxy, cyano or nitro or, taken together, methylenedioxy.

Examples of compounds to which the invention relates are 2-(2-Picolylseleno)-N-(2-pyridyl)benzamide 2-(2-Picolylseleno)-N-(4-pyridyl)benzamide dihydrochloride 2-(3-Picolylseleno)-N-(2-pyridyl)benzamide 2-(4-Picolylseleno)-N-(2-pyridyl)benzamide 2-(4-Picolylseleno)-N-(3-pyridyl)benzamide 2-(4-Picolylseleno)-N-(4-pyridyl)benzamide 2-(2-Picolylseleno)-N-(3-pyridyl)benzamide hydrochloride 2-(2-Picolylseleno)-N-(3-pyridyl)benzamide dihydrochloride 2-(3-Picolylseleno)-N-(3-pyridyl)benzamide dihydrochloride 2-(3-Picolylseleno)-N-(4-pyridyl)benzamide dihydrochloride 2-(2-Picolylseleno)-N-(2-pyridyl)benzamide 2-(2-Picolylseleno)-N-(3-pyridyl)benzamide 2-(3-Picolylseleno)-N-(3-pyridyl)benzamide N-Phenyl-2-(2-picolyseleno)benzamide N-Phenyl-2-(3-picolyseleno)benzamide N-Phenyl-2-(4-picolyseleno)benzamide N-(4-Chlorophenyl)-2-(4-picolylseleno)benzamide and N-(4-Fluorophenyl)-2-(4-picolylseleno)benzamide.

The compounds to which the invention relates can be prepared via the isolable 2-(picolylseleno)benzoic acids. Suitable for this purpose are, for instance:

2-(2-Picolylseleno)benzoic acid 2-(3-Picolylseleno)benzoic acid 2-(4-Picolylseleno)benzoic acid The 2-(picolylseleno)benzoic acids can either be reacted with bis [2-oxo-3-oxazolidinyl]phosphoryl chloride and an aniline or pyridine-containing amine in a chlorinated hydrocarbon to yield the products to which the invention relates (reaction scheme 1) or the reaction can be carried our with 2-chloro-1-methylpyridinium iodide and a pyridine-containing amine to yield the product to which the invention relates (reaction scheme 2).

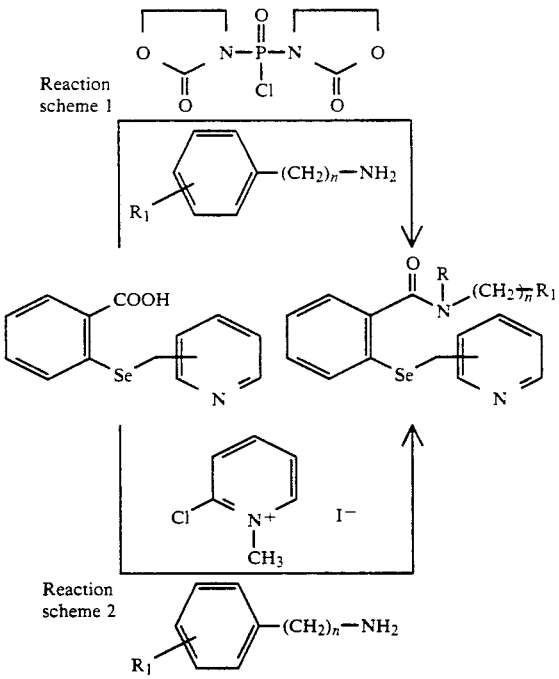

The compounds of Formula I can also be prepared by reacting the picolylselenobenzoic acids with chloromethylenedimethyliminium chloride and a pyridine-containing amine or an aniline and separating the product from the reaction mixture.

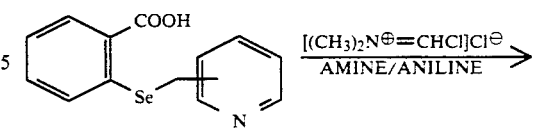

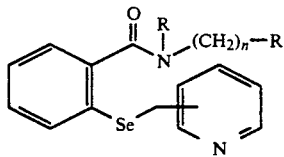

The picolylselenobenzoic acids are prepared by reducing diselenosalicylic acid with sodium dithionite in caustic soda solution, then reacting with picolyl chloride hydrochloride in aqueous solution and isolating the completed product from the reaction mixture:

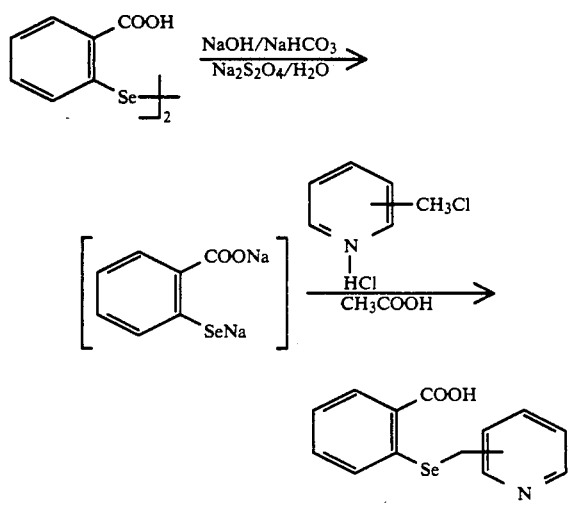

The compounds of the invention can be used as antiinflammatories in oral, rectal, parenteral, topical, intravenous and intramuscular administration.

This invention also relates to pharmaceutical products containing compounds according to Formula I as active ingredients. Pharmaceutical products to which the invention relates are enteral as well as oral, rectal or parenteral dosage forms which contain the pharmaceutically active ingredients either alone or together with a usual, pharmaceutically employed excipient. The pharmaceutical preparations of the active ingredient should preferably take the form of individual doses, which are adapted to the desired method of administration, such as, for example, tablets, dragees, capsules, suppositories, granules, solutions, emulsions or suspensions. The dosage of substance usually lies between 10 and 1000 mg/day preferably between 30 and 300 mg/day and can be administered in one does or distributed over several doses, preferably two or three doses daily. It has been found that these pharmaceutical products have excellent inflammation inhibiting characteristics.

The preparation of the substances, to which the invention relates, will be elucidated in greater detail in the examples that follow. The melting points quoted were determined using a Büchi 510 melting point determination apparatus, are quoted in °C. and have not been corrected.

EXAMPLE 1

2-(2-Picolylseleno)benzoic acid

To a stirred suspension of 10 g (0.025 mol) diselenosalicylic acid in 75 ml water is added 7.6 g (0.19 ml) sodium hydroxide, when the internal temperature rises slightly and the acid goes into solution. Then 20 g (0.189 mol) sodium carbonate and 11.6 g (0.067 mol) sodium dithionite are added with slight heating, followed by 2 h heating under reflux. After cooling to room temperature 9.8 g (0.06 mol) 2-picolyl chloride hydrochloride dissolved in 20 ml water are added dropwise and stirring is continued at room temperature for 14 h. Then 25% hydrochloric acid is added to adjust to pH 8 to 9 followed by acetic acid (98%) to pH 5–6. The precipitated white crude product is sucked off, washed neutral with water and recrystallized from 2-propanol (900 ml).

Yield 10.5 g (71.9% of th.)
mp 220°–221° C.

EXAMPLE 2

2-(3-Picolylseleno)benzoic acid

Repeating the procedure in Example 1 but using 9.8 g (0.06 mol) 3-picolyl chloride hydrochloride yields as product 2-(3-picolylseleno)benzoic acid which, after the reaction, is recrystallized from 660 ml methanol.

Yield 9.5 g (65% of th.)
mp 237° C.

EXAMPLE 3

2-(4-Picolylseleno)benzoic acid

Repeating the procedure in Example 1 but using 9.8 g (0.06 mol) 4-picolyl chloride hydrochloride yields as product 2-(4-picolylseleno)benzoic acid. Recrystallization is carried out from 250 ml methanol.

Yield 10.8 g (74% of th.)
mp 243°–245° C.

EXAMPLE 4

2-(2-Picolylseleno)-N-(2-pyridyl)benzamide

To a solution of 5.84 g (0.02 mol) 2-(2-picolylseleno)-benzoic acid (from Example 1) in 40 ml dichloromethane that has been cooled to 0° C. are added in one portion 5 g (0.02 mol) bis[2-oxo-3-oxazolidinyl]phosphoryl chloride. After stirring for 2 hours at room temperature 1.88 g (0.02 mol) 2-aminopyridine, 50 ml dichloromethane and 6.4 ml triethylamine are added dropwise in succession at 10° C. and stirring is continued at room temperature for 20 h. The reaction mixture is extracted twice with 100 ml portions of water, dried over sodium sulfate and the solvent removed. The brown oil (7 g) is taken up in 100 ml 1 N HCl, filtered, the filtrate basified with 13 ml 10 N sodium hydroxide and extracted with 100 ml ethyl acetate. The organic phase is dried, concentrated and the solid residue obtained is stirred for 48 h with 100 ml diethyl ether. After filtration the crude product is cleaned up by column chromatography (silica gel/dichloromethane) and recrystallized from 20 ml 2-propanol.

Yield 1.0 g (13.6% of th.)
mp 139°–140° C.

EXAMPLE 5

2-(2-Picolylseleno)-N-(4-pyridyl)benzamide dihydrochloride

A solution of 4 g (0.0137 mol) 2-(2-picolylseleno)benzoic acid from Example 1 and 2 ml triethylamine in 40 ml dichloromethane is treated with 3.5 g (0.0137 mol) 2-chloro-1-methylpyridinium iodide and stirred at room temperature for 1 hour. Then a solution of 1.29 g (0.0137 mol) 4-aminopyridine and 2 ml triethylamine in 30 ml dichloromethane are added dropwise within 15 min and after stirring for 2 hours the reaction mixture is extracted once with 100 ml 1 N sodium hydroxide solution and twice with 100 ml portions of water. The organic phase is dried, the solvent removed and the residue taken up in 2-propanol (80 ml)/15% HCl (10 ml). After filtration the solid crude product is dissolved in 100 ml methanol and diethyl ether is added dropwise until the solution remains turbid. The crystals which then form are filtered off after 2 hours and dried.

Yield 3.9 g (70.9% of th.)
mp 228°–230° C.

EXAMPLE 6

2-(2-Picolylseleno-N-(4-pyridyl)benzamide

A solution of 0.5 g (0.00113 mol) 2-(2-picolylseleno)-N-(4-pyridyl)benzamide dihydrochloride from Example 5 in 2 ml $H_2O$ is made alkaline with 10 N NaOH and extracted twice with 5 ml portions of dichloromethane. The organic phase is dried over magnesium sulfate, the solvent removed and the crude product recrystallized from 15 ml 2-propanol.

Yield 0.40 g (96% of th.)
mp 136°–137° C.

EXAMPLE 7

2-(2-Picolylseleno)-N-(3-pyridyl)benzamide hydrochloride

To a solution of 3 g (0.0103 mol) 2-(2-picolylseleno)-benzoic acid (from Example 1) in 20 ml dichloromethane that has been cooled to −10° C. is added with stirring 1.32 g (0.0103 mol) chloromethylenedimethyliminium chloride, the mixture is then stirred at room temperature for 2 hours then a solution of 0.97 g (0.0103 mol) 3-aminopyridine and 2.32 g (0.023 mol) triethylamine in 20 ml dichloromethane are added dropwise with in 10 minutes and stirring is continued at room temperature for 14 hours, the reaction mixture is extracted with 50 ml water and the separated dichloromethane phase is dried and the solvent removed. The oily residue is treated with 50 ml 1 N HCl and filtered, it is then basified with NaOH (5%) and extracted twice with 50 ml portions of dichloromethane. The organic phase is dried over sodium sulfate and the solvent removed, the residue is dissolved in 40 ml 2-propanol and treated slowly with stirring with 15 ml 2-propanol/10% HCl when the hydrochloride crystallizes out. This is washed with 50 ml diethyl ether.

Yield 1.85 g (44.4% of th.)
mp 221°–222° C.

EXAMPLE 8

2-(2-Picolylseleno)-N-(3-picolyl)benzamide dihydrochloride

Repeating the procedure in Example 7 but using 3.0 g (0.0103 mol) 2-(2-picolylseleno)benzoic acid (Example 1) and 1.11 g (0.0103 mol) 3-picolylamine yield as product 2-(2-picolylseleno)-N-(3-picolyl)benzamide dihydrochloride.

Yield 3.1 g (66.3% of th.)
mp 193°–195° C.

EXAMPLE 9

2-(3-Picolylseleno)-N-(4-pyridyl)benzamide dihydrochloride

To a solution of 4 g (0.0132 mol) 2-(3-picolylseleno)-benzoic acid (from Example 2) and 4.4 ml triethylamine in 40 ml dichloromethane, that has been cooled to 0° C., is added in one portion 3.5 g (0.0132 mol) bis(2-oxo-3-oxazolidinyl)-phoshoryl chloride. After 15 minutes 1.3 g (0.0138 mol) 4-aminopyridine is added and the mixture stirred at 0° C. for 3.5 hours. It is then extracted twice with 100 ml portions of water, the organic phase dried over sodium sulfate and the solvent removed. The residue is taken up in 60 ml 2-propanol and treated with 10 ml 15% HCl in 2-propanol. The solid product that results is dissolved in 50 ml $H_2O$ and treated with 1 g active charcoal, stirred at room temperature for 15 minutes and then filtered. Acetone is added dropwise to the filtrate until the solution remains turbid. The crystals that are formed are filtered off after 2 hours and dried.

Yield 1.3 g (21.5% of th.)
mp 249°–254° C.

EXAMPLE 10

2-(3-Picolylseleno)-N-(3-pyridyl)benzamide dihydrochloride

A suspension of 4 g (0.0137 mol) 2-(3-picolylseleno)-benzoic acid from Example 2 in 40 ml dichloromethane is treated at +5° C. under stirring with 1.76 g (0.0137 mol) chloromethylenedimethyliminium chloride (Vilsmeier's reagent) and stirred for 2 hours at room temperature. A solution of 1.29 g (0.0137 mol) 3-aminopyridine and 3.2 ml triethylene in 30 ml dichloromethane is then added dropwise and stirred for 2 h. The reaction mixture is diluted with 100 ml dichloromethane and extracted twice with 100 ml portions of water, the organic phase is dried over sodium sulfate, the solvent removed and the oily residue is dissolved in 140 ml 2-propanol. The solution is taken up in 10 ml 15% HCl (in 2-propanol), the crude product so obtained is stirred for 30 minutes with 20 ml 1 N NaOH and extracted twice with 100 ml portions of ethyl acetate. The organic phase is washed with 200 ml water, dried and the solvent removed. The viscous residue is taken up in 100 ml 2-propanol). The solid crude product is dissolved in 100 ml methanol and diethyl ether is added dropwise until the solution remains turbid. The crystals that precipitate out are filtered off after 2 h and dried.

Yield 2.3 g (41% of th.)
mp 261°–263° C.

EXAMPLE 11

N-Phenyl-2-(2-picolylseleno)benzamide

To a solution of 7 g (0.024 mol) 2-(2-picolylseleno)-benzoic acid (from Example 1) and 2.4 g (0.024 mol) triethylamine in 40 ml dichloromethane which has been cooled to 0°–5° C. is added 6 g (0.024 mol) bis(2-oxo-3-oxazolidinyl)phosphoryl chloride in solid form as one portion. After stirring for 20 minutes a solution of 2.2 g (0.024 mol) aniline in 5 ml dichloromethane and a solution of 2.4 g (0.024 mol) triethylamine in 5 ml dichloromethane and a solution of 2.4 g (0.024 mol) triethylamine in 5 ml dichloromethane are added dropwise within 5 min, after 16 h at room temperature the reaction mixture is washed with 100 ml water. The organic phase is extracted successively with 100 ml 10% $NaHCO_3$ solution, 100 ml 10% citric acid and 100 ml water. The organic phase is dried over sodium sulfate and the solvent removed under water pump vacuum. The solid crude product (6.3 g) is recrystallized from 35 ml 2-propanol.

Yield 4.8 g (54.4% of th.)
mp 135.5°-136° C.

EXAMPLE 12

N-Phenyl-2-(3-picolylseleno)benzamide

Repeating the procedure in Example 11 but using 7.0 g (0.024 mol) 3-picolylselenobenzoic acid (from Example 2) yields a crude product which is cleaned up by column chromatography (silica gel; dichloromethane:-methanol 99:1; fractions of 50 ml) The solvent is removed from fractions 48 to 128 under water pump vacuum and the solid crude product recrystallized from 50 ml 2-propanol.

Yield 4.5 g (51% of th.)
mp 136°-137° C.

EXAMPLE 13

N-Phenyl-2-(4-picolylseleno)benzamide

Repeating the procedure in Example 11 but using 7.0 g (0.024 mol) 4-picolylselenobenzoic acid (from Example 3) yields a crude product which is cleaned up by column chromatography (silica gel; dichloromethane:-methanol 99:1; fractions of 50 ml) The solvent is removed from fractions 74 to 104 under water pump vacuum and the solid crude product recrystallized from 50 ml 2-propanol.

Yield 3.6 g (41% of th.)
mp 166°-167° C.

EXAMPLE 14

N-(4-Chlorophenyl-2-(4-picolylseleno)benzamide

Repeating the procedure in Example 11 but using 3.1 g (0.024 mol) 4-chloroaniline yields a crude product which is triturated in a mixture of 10 ml 2-propanol and 5 ml n-hexane and then recrystallized twice from 30 ml portions of 2-propanol.

Yield 1.7 g (18% of th.)
mp 157°-158° C.

EXAMPLE 15

N-(4-Fluorophenyl-2-(4-picolylseleno)benzamide

Repeating the procedure in Example 11 but using 2.7 g (0.024 mol) 4-fluoroaniline yields a crude solid product which is recrystallized twice from 30 ml portions of 2-propanol.

Yield 2.6 g (28% of th.)
mp 152.5°-153.5° C.

We claim:

1. A compound or a pharmaceutically acceptable salt thereof according to the Formula (I)

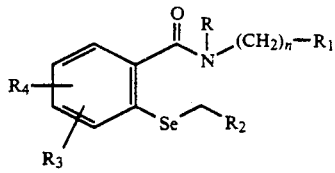

wherein
R is hydrogen, methyl or ethyl,
$R_1$ is a 2-pyridyl, 3-pyridyl or 4-pyridyl group or is phenyl, chlorophenyl or fluorophenyl,
$R_2$ is a 2-pyridyl, 3-pyridyl or 4-pyridyl group,
$R_3$ and $R_4$ are identical or different and, taken separately, are hydrogen, fluorine, chlorine, bromine, $C_1$ to $C_4$ alkyl, $C_1$ to $C_4$ alkoxy, hydroxy, cyano or nitro or, taken together, are methylenedioxy, and n is 0 or 1.

2. The compound of the Formula (I) defined in claim 1 selected from the group consisting of:
2-(2-picolylseleno)-N-(2-pyridyl)benzamide,
2-(2-picolylseleno)-N-(4-pyridyl)benzamide,
2-(2-picolylseleno)-N-(3-pyridyl)benzamide,
2-(2-picolylseleno)-N-(3-picolyl)benzamide; and
2-(3-picolylseleno)-N-(3-pyridyl)benzamide, or a pharmaceutically acceptable salt thereof.

3. 2-(2-picolylseleno)-N-(3-pyridyl)benzamide or a pharmaceutically acceptable salt thereof as defined in claim 1.

4. A compound selected from the group which consists of:
2-(2-picolylseleno)benzoic acid;
2-(3-picolylseleno)benzoic acid; and
2-(4-picolylseleno)benzoic acid.

5. 2-(2-picolylseleno)benzoic acid as defined in claim 4.

6. An anti-inflammatory pharmaceutical composition which comprises as active ingredient a therapeutically effective amount of a compound of the Formula (I) as defined in claim 1 or a pharmaceutically acceptable salt thereof in combination with a pharmaceutically acceptable inert carrier.

7. An anti-inflammatory method of treatment which comprises administering to a subject susceptible to inflammation a therapeutically effective amount of the compound of the Formula (I) defined in claim 1 or a pharmaceutically acceptable salt thereof.

* * * * *